United States Patent [19]

Asayama et al.

[11] Patent Number: 4,568,443
[45] Date of Patent: Feb. 4, 1986

[54] AIR-TO-FUEL RATIO SENSOR

[75] Inventors: Yoshiaki Asayama, Himeji; Seiya Kominami, Takasago, both of Japan

[73] Assignees: Mitsubishi Denki Kabushiki Kaisha, Tokyo; NGK Spark Plug Co., Ltd., Nagoya, both of Japan

[21] Appl. No.: 647,663

[22] Filed: Sep. 6, 1984

[51] Int. Cl.$^4$ ............................................. G01N 27/58
[52] U.S. Cl. .................... 204/410; 204/412; 204/425; 204/426
[58] Field of Search ................ 204/410, 412, 426, 1 S, 204/425

[56] References Cited

U.S. PATENT DOCUMENTS

| | | | |
|---|---|---|---|
| 3,400,054 | 9/1968 | Ruka et al. | 204/1 R |
| 3,907,657 | 9/1975 | Heijne et al. | 204/1 S X |
| 4,088,543 | 5/1978 | Ruka | 204/1 S |
| 4,158,166 | 6/1979 | Isenberg | 204/426 X |
| 4,272,329 | 6/1981 | Hetrick et al. | 204/1 S |
| 4,272,330 | 6/1981 | Hetrick | 204/1 S |
| 4,272,331 | 6/1981 | Hetrick | 204/1 S |
| 4,384,935 | 5/1983 | DeJong | 204/406 |
| 4,396,466 | 8/1983 | Hetrick et al. | 204/1 S |
| 4,450,065 | 5/1984 | Yamada et al. | 204/412 |

FOREIGN PATENT DOCUMENTS

| | | | |
|---|---|---|---|
| 1810458 | 6/1969 | Fed. Rep. of Germany | 204/410 |
| 2654483 | 7/1977 | Fed. Rep. of Germany | 204/426 |

Primary Examiner—G. L. Kaplan
Attorney, Agent, or Firm—Oblon, Fisher, Spivak, McClelland & Maier

[57] ABSTRACT

An air-to-fuel ratio sensor of a construction, wherein an oxygen concentration cell having a chamber, at least one side of which is communicative with the atmosphere and an oxygen pump are disposed in mutual confrontation through a clearance chamber, or a spatial chamber having a tiny hole for dispersion, and gas to be measured is introduced into this clearance chamber or the spatial chamber to measure its air-to-fuel ratio from an output of the oxygen concentration cell or a control quantity of the oxygen pump, thereby making it possible to control the internal combustion engine over a wide range other than its theoretical air-to-fuel ratio.

6 Claims, 8 Drawing Figures

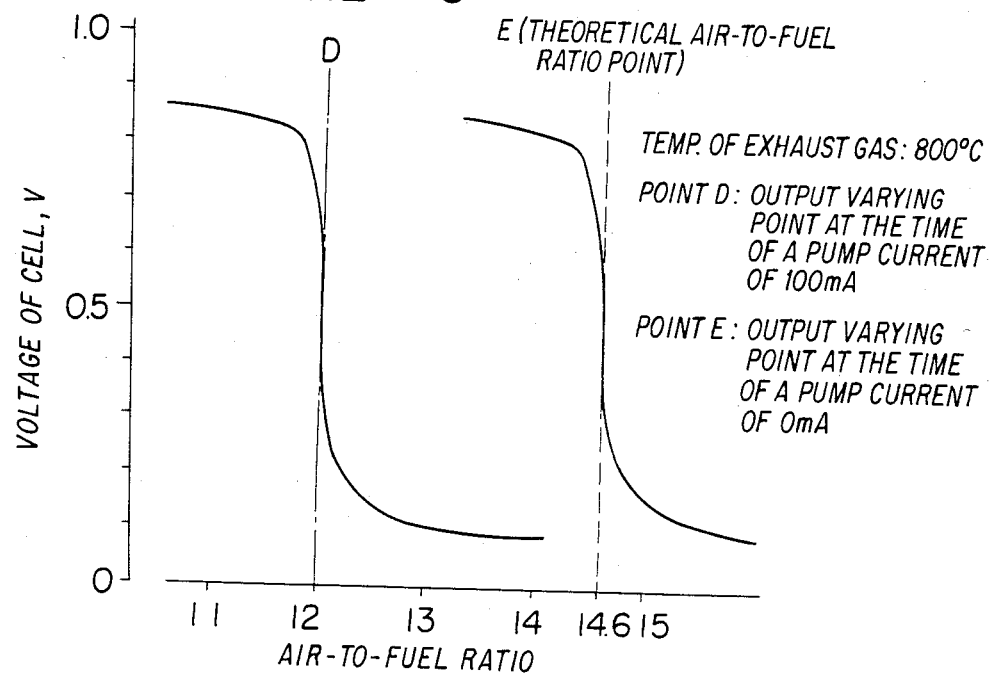
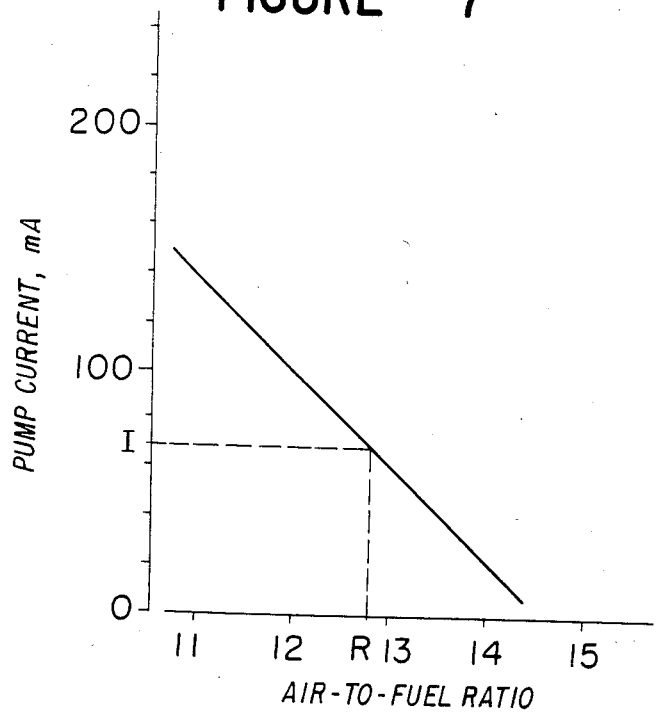

AIR-TO-FUEL RATIO SENSOR

BACKGROUND OF THE INVENTION

This invention relates to an air-to-fuel sensor for measuring a ratio of air to fuel, i.e., an air-to-fuel ratio in exhaust gas of an internal combustion engine, as an example.

As the air-to-fuel ratio sensing element, a zirconia-oxygen concentration cell sensor has so far been used. This sensor detects the state of combustion of the fuel at its theoretical air-to-fuel ratio in utilization of the fact that an output voltage abruptly varies at a theoretical air-to-fuel ratio point. For instance, the sensor is utilized in a system which controls the internal combustion engine for automobile in such a manner that it may be operated at the theoretical air-to-fuel ratio. With the above-mentioned oxygen sensor, however, there is no substantial change in the electromotive force in a rich atmosphere with the consequence that precise measurement of the air-to-fuel ratio at the rich side is impossible. Therefore, with a view to maintaining a substantially constant rich atmosphere, various devices have been provided at the side of the air intake system to effect the open control. With such control systems, however, there exist disadvantages such that the air-to-fuel ratio control becomes costly and the high precision control cannot be done.

Also, as the sensor for detecting the entire range of the air-to-fuel ratio, there have been proposed various sensors as described in Japanese Patent Publications No. 34077/1978 and No. 49860/1982, although none of them has yet attained a stage of being practically useful owing to technical difficulty involved. In the above-mentioned Japanese Patent Publication No. 34077/1978, there is described an oxygen sensor of a type, in which non-catalytic electrodes made of a material such as gold, silver, etc. are used as the measuring electrodes to be positioned in the exhaust gas in a zirconia tube, for measuring the air-to-fuel ratio at the rich side from the theoretical air-to-fuel ratio point. However, even the above-mentioned electrodes have the catalytic function, on account of which the gas adsorption phenomenon takes place, the reproducibility of the output voltage is poor, and, further, durability of the electrode in the gas at a high temperature and a high speed is poor, hence the sensor cannot be used practically. Furthermore, the Japanese Patent Publication No. 49860/1982 describes a method, by which the air-to-fuel ratio at both rich and lean sides can be measured. However, even this method has various disadvantages such that the current value in use is extremely low, which requires care in the electrical treatment, the art of manufacturing is difficult, and durability and response of the electrode are poor in the gas atmosphere at a high temperature and a high speed, or various other disadvantages.

SUMMARY OF THE INVENTION

The present invention has been made with a view to removing these disadvantages inherent in the conventional air-to-fuel ratio sensor as described above, and aims at providing an improved sensor which is comparatively cheap and excellent in practicability.

The present invention is also directed to provide a sensor which measures an air-to-fuel ratio in the exhaust gas for the closed control of the air-to-fuel ratio of both rich-burn engine and lean-burn engine for improvement in the combustion efficiency of the automobile engine, and non-toxicity of the exhaust gas.

That is to say, the air-to-fuel ratio sensor according to the present invention is so constructed that electrochemical devices in the form of a solid electrolytic oxygen pump and a solid electrolytic oxygen concentration cell, both being made up by attaching electrodes onto both surfaces of the solid electrolytic plate, are disposed in mutual confrontation through a clearance chamber or a spatial chamber so as to introduce measuring gas into the chamber, while forming an air chamber to be communicative with the atmosphere on the side surface of at least one of the above-mentioned oxygen pump and the oxygen concentration cell opposite to the above-mentioned chamber so as to enable oxygen in the air to be utilized as the oxygen feeding source.

According to the present invention, in one aspect of it, there is provided an air-to-fuel ratio sensor, which comprises in combination: an oxygen pump of a construction, wherein electrodes are provided on both side surfaces of a solid electrolytic plate, and an electric voltage is applied to said electrodes; an oxygen concentration cell of a construction, wherein electrodes are provided on both side surfaces of a solid electrolytic plate, and an output current is taken out of said electrodes; and a spatial chamber covering one of said electrodes of said oxygen pump and one of said electrodes of said oxygen concentration cell disposed in opposition to said electrode, and having a tiny hole or a clearance for introducing gas to be measured, the side surface of at least one of said oxygen pump and said oxygen concentration cell opposite to said spatial chamber being made communicative with the atmosphere.

According to the present invention, in another aspect of it, there is provided an air-to-fuel ratio sensor, which comprises in combination: oxygen quantity control and feeding means to feed a determined quantity of oxygen; chemical equivalent point detecting means; and a clearance chamber, or a spatial chamber having a tiny hole for dispersion, into which an arbitrary quantity of gas to be measured is introduced and measured by said both means, the oxygen concentration of said measuring gas in said chamber being controlled by said oxygen quantity control and feeding means so that the measuring gas in said chamber attains the chemical equivalent point at a desired air-to-fuel ratio, and the air-to-fuel ratio of the measuring gas outside said chamber being measured by an output signal from said chemical equivalent point detecting means.

According to the present invention, in still another aspect of it, there is provided an air-to-fuel ratio sensor, which comprises in combination: oxygen quantity control and feeding means to feed a predetermined quantity of oxygen; chemical equivalent point detecting means; and a clearance chamber, or a spatial chamber having a tiny hole for dispersion, into which an arbitrary quantity of gas to be measured is introduced and measured by said both means, the oxygen concentration of said measuring gas in said chamber being controlled by said oxygen quantity control and feeding means so that the measuring gas in said chamber attains the chemical equivalent point at a desired air-to-fuel ratio, and the air-to-fuel ratio of the measuring gas outside said chamber being measured by an output signal corresponding to the control quantity of said oxygen quantity control and feeding means.

BRIEF DESCRIPTION OF THE DRAWINGS

The foregoing objects, other objects as well as the specific construction and function of the air-to-fuel ratio sensor according to the present invention will become more apparent and understandable from the following detailed description thereof, when read in conjunction with the accompanying drawings.

In the accompanying drawings:

FIG. 6 is a graphical representation showing characteristic variations in voltage of the oxygen concentration cell, when the pump current is varied;

FIG. 7 is a characteristic diagram indicating points of variations in the output of the oxygen concentration cell in terms of the pump current and the air-to-fuel ratio.

DETAILED DESCRIPTION OF THE PREFERRED EMBODIMENTS

In the following, the present invention will be explained in detail in reference to the preferred embodiment thereof shown in the accompanying drawings.

EXAMPLE 1

Two sheets of thin plates, each having a dimension of 5 mm×20 mm×0.5 mm were cut out of a $ZrO_2$ baked body which was stabilized with 10% by weight of $Y_2O_3$. Then, on both surfaces of each plate, platinum was vapor-deposited to a thickness of approximately 2,000 Å in a size of 3 mm×4 mm, followed by electroplating of electrodes to a thickness of 1 micron, thereby fabricating the solid electrolytic plate 12a (12b) having the electrodes 15a, 15b (16a, 16b) thereon, as shown in FIG. 2.

Figure 3:
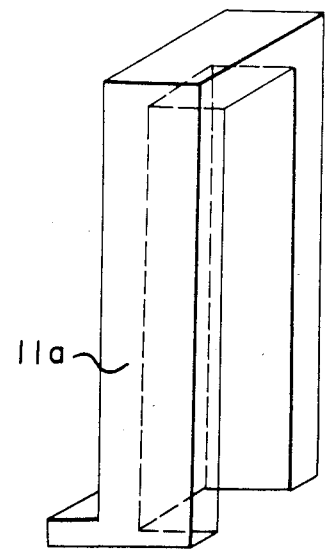
FIG. 3 is also a perspective view of another solid electrolytic plate.

In the next place, two sheets of plates, each having a dimension of 5 mm×20 mm×1.5 mm were cut out of the same material, and made into the solid electrolytic plate 11a (11b), as shown in FIG. 3, having a recess to form an opening to be communicative with the atmosphere side, when it is fastened together with the above-mentioned solid elecrolytic plate 12a (12b).

Figure 4:
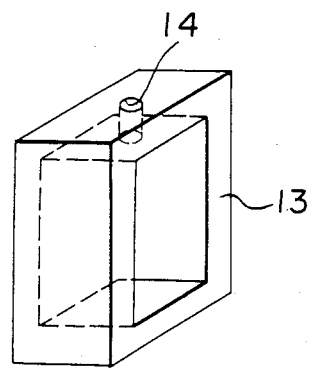
FIG. 4 is a perspective view of a spacer.

Further, a plate of 5 mm×5 mm×1.5 mm was cut out of the same material which was then provided with an opening of 4 mm×4 mm to form a spatial chamber, and further perforated with a hole of 0.075 mm in diameter to be a tiny hole 14 for dispersion, thereby fabricating a spacer 13 which is a hollow body having open oppposite sides as shown in FIG. 4.

Figure 1:
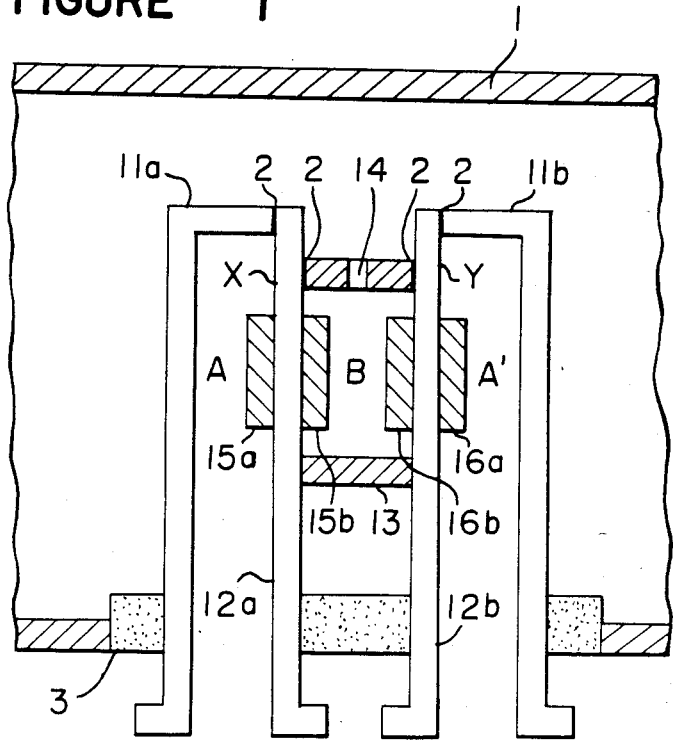
FIG. 1 is a longitudinal cross-sectional view of the air-to-fuel ratio sensor according to the present invention.
Figure 2:
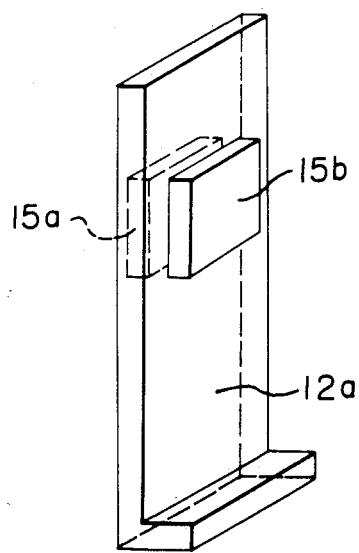
FIG. 2 is a perspective view of a solid electrolytic plate having electrodes on both side surfaces.

The above-mentioned members in FIGS. 2, 3 and 4 were assembled through a holding member 3 within an exhaust pipe 1 as shown in FIG. 1 with glass frit 2 of NaO-$SiO_2$-$Al_2O_3$ series and exhibiting its softening point at a temperature of 1,000° C. having been applied to the joining part of each of the members to be fastened together, after which the assembly was heated in a furnace at 1,150° C. and fastened together.

In the following, the function of the sensor as constructed in the above-described manner will be explained in reference to FIG. 1. In the drawing, a zirconia solid electrolytic oxygen pump X as the oxygen quantity control and feeding means is made up of the solid electrolytic plates 11a, 12a. Further, a zirconia solid electrolytic oxygen concentration cell Y as the chemical equivalent point detecting means is constructed with the solid electrolytic plates 11b, 12b. The spacer 13 forms the spatial chamber B provided with a tiny hole 14 for dispersion, through which a gas is introduced into it and measured. When a voltage is applied to the elecrodes 15a, 15b of the above-mentioned oxygen pump X, oxygen in the reference air chamber A which is open to the atmospheric side moves into the spatial chamber B. Also, the above-mentioned oxygen concentration cell Y generates an output voltage in accordance with the oxygen concentration in the air chamber A' which is open to the atmospheric side so as to enable the air to be utilized as the reference gas, and the oxygen concentration in the above-mentioned spatial chamber B. This output voltage E can be represented by the well-known Nernst equation, as shown in the following:

$$E = \frac{RT}{4F} \ln \frac{PO''_2}{PO_2}$$

(where: R denotes gas constant; T represents absolute temperature; F indicates Faraday constant; $PO_2$ denotes partial pressure of oxygen in the reference gas; and $PO''_2$ represents partial pressure of oxygen in the gas to be measured).

By the way, it has been known that, at the rich side of the air-to-fuel ratio from the theoretical air-to-fuel ratio point, the gas to be measured has an extremely low oxygen concentration, while inflammable gas abruptly increases, on account of which the output voltage from the zirconia solid electrolytic oxygen concentration cell abruptly changes at the theoretical air-to-fuel ratio point, and that, in utilization of this phenomenon, the zirconica solid electrolytic oxygen concentration cell is used as the means for detecting the theoretical air-to-fuel ratio point. The present invention makes it possible to accurately measure not only the theoretical air-to-fuel ratio, but also the air-to-fuel ratio when it is at either the rich side or lean side from the theoretical air-to-fuel ratio.

Referring now to FIGS. 6 and 7, explanations will be given as to the measuring means of the air-to-fuel ratio, when it is at the rich side from the theoretical air-to-fuel ratio.

By the action of the oxygen pump X, the oxygen concentration in the above-mentioned spatial chamber B becomes high. However, since the gas to be measured in the above-mentioned spatial chamber B is so controlled that the chemical equivalent point may be reached, the chemical equivalent point of the measuring gas outside the spatial chamber B shifts substantially to the rich side.

Since this shifting quantity can be freely controlled by the quantity of oxygen as introduced into chamber B, an arbitrary air-to-fuel ratio can be detected.

FIG. 6 is a graphical representation showing variations in output from the oxygen concentration cell Y in the case of the exhaust gas being at 800° C. and the pump current being 0 mA and 100 mA. From this graphical representation, it will be seen that, at the pump current of 0 mA, the output varies remarkably at the theoretical air-to-fuel ratio of 14.6 owing to the characteristic of the sensor, and, when the pump current of 100 mA is caused to flow, the oxygen concentration in the spatial chamber B increases, whereby the output varying point shifts to the air-to-fuel ratio of 12. And, it has been verified that the magnitude of the pump current and the air-to-fuel ratio, when the output varies remarkably, takes a relationship as shown in FIG. 7.

Accordingly, if and when the pump current is varied, and the point, at which the output from the oxygen concentration cell Y varies largely, can be verified as I, the air-to-fuel ratio at that time can be known as R from the characteristic diagram in FIG. 7.

Figure 8:
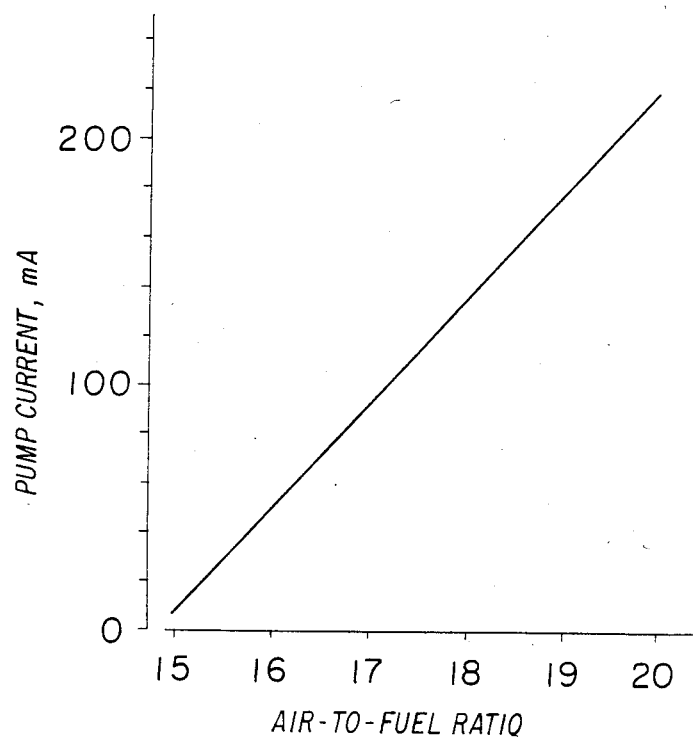
FIG. 8 is a characteristic diagram showing a relationship between the pump current and the air-to-fuel ratio at the lean side.

Furthermore, in the case of the air-to-fuel ratio being at the lean side from the theoretical air-to-fuel ratio, the air-to-fuel ratio can be measured in the following manner. When the function of the solid electrolytic oxygen pump X is reversed (i.e., the voltage to be applied is reversed) to discharge the oxygen in the spatial chamber B, and the measurement was conducted by varying the pump current in correspondence to the air-to-fuel ratio so that the output voltage from the solid electrolytic oxygen concentration cell Y may become 100 mV, i.e., partial pressure of oxygen in both the spatial chamber B and the reference air chamber A' may assume predetermined values, the characteristic as shown in FIG. 8 could be verified at the discharge gas temperature of 800° C. From this characteristic, it has been found that, for measurement of the air-to-fuel ratio at the lean side, the pump current may be measured.

EXAMPLE 2

Two sheets of thin plates, each having a dimension of 5 mm×20 mm×0.5 mm were cut out of a $ZrO_2$ baked body which was stabilized with 10% by weight of $Y_2O_3$. Then, on both surfaces of each plate, platinum was vapor-deposited to a thickness of approximately 2,000 A, followed by electroplating of electrodes to a thickness of 1 micron, thereby fabricating the solid electrolytic plate 12a (12b) having the electrodes thereon.

In the next place, two sheets of plates, each having a dimension of 5 mm×20 mm×1.5 mm were cut out of the same material, and made into the solid electrolytic plate 11a (11b) having a recess to form an opening to be communicative with the atmospheric side, after which they are joined together with the above-mentioned solid electrolytic plate 12a (12b).

Further, a plate having a dimension of 5 mm×5 mm×0.075 mm was cut out of the same material to be used as the spacer 4 for a clearance chamber C.

Figure 5:
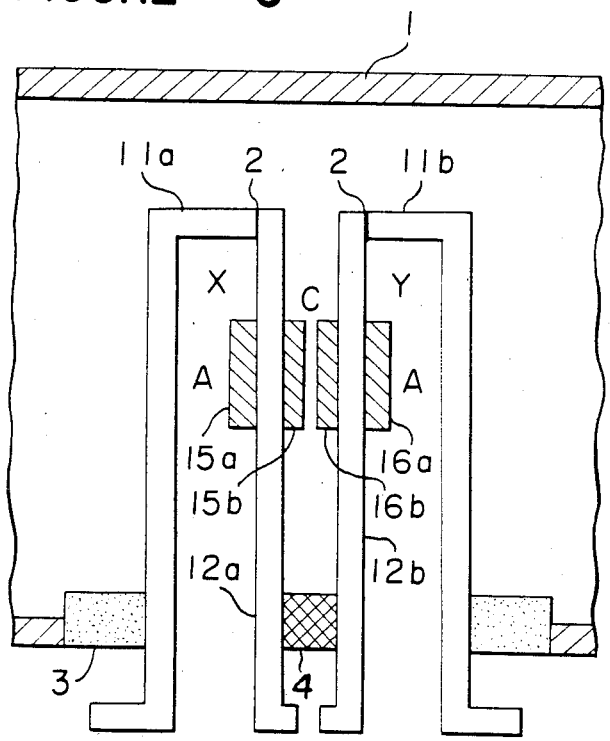
FIG. 5 is a longitudinal cross-sectional view showing another embodiment of the air-to-fuel ratio sensor according to the present invention.

The above-mentioned members were assembled in a manner as shown in FIG. 5 so that the solid electrolytic plates 12a, 12b may be arranged in contiguity each other, then glass frit of $NaO-SiO_2-Al_2O_3$ series and exhibiting its softening point at 1,000° C. was applied onto the joining part of each of the members to be fastened together, after which the assembly was heated in a furnace at 1,150° C. and fastened together.

The thus constructed sensor exhibited the same function as that in Example 1 above, wherein the spatial chamber B is provided with a tiny hole 14 for dispersion, and its output characteristic was also same.

Although, in the foregoing, the present invention has been described with reference to preferred embodiments thereof, the invention is not restricted by these exmaples alone, but any changes and modifications may be made by those persons skilled in the art within the spirit and scope of the invention as recited in the appended claims.

We claim:
1. An air-to-fuel ratio sensor, which comprises in combination:
 (a) an oxygen pump having electrodes provided on both side surfaces of a first solid electrolytic plate, wherein an electric voltage is applied to said electrodes;
 (b) an oxygen concentration cell having electrodes provided on both side surfaces of a solid electrolytic plate, wherein an output current is taken out of said electrodes, and wherein said oxygen pump and said osygen concentration cell are constructed with said first solid electrolytic plate in a planar form with the electrodes being provided on both surfaces thereof and with a second solid electrolytic plate in a box shape with an end surface thereof being opposed to said first solid electrolytic plate and being opened in one direction; and
 (c) a chamber having a tiny hole or a clearance for gas to be measured, said chamber including one of said electrodes of said oxygen pump and one of said electrodes of said oxygen concentration cell disposed in opposition to one another,
 the side surface of at least one of said oxygen pump and said oxygen concentration cell opposite to said chamber being made communicative with a source of atmospheric air.

2. The air-to-fuel ratio sensor according to claim 1, wherein said chamber for introduction of gas to be measured is formed by a hollow body having open opposite side surfaces and having at least one tiny hole on a top surface thereof.

3. The air-to-fuel ratio sensor according to claim 1, wherein said first solid electrolytic plates constituting said oxygen pump and said oxygen concentration cell are disposed closely adjacently to one another, and one side surface of each of said first solid electrolytic plates face one another to form said chamber into which gas to be measured is introduced.

4. The air-to-fuel ratio sensor according to claim 3 including a holding member surrounding said oxygen pump and oxygen concentration cell, said holding member being bonded to said cells for supporting said cells within an exhaust pipe.

5. The air-to-fuel ratio sensor according to claim 4 wherein a portion of said holding member positioned between said facing side surfaces is formed of a solid electrolytic plate and defines a portion of said chamber.

6. The air-to-fuel ratio sensor according to claim 1 including a holding member surrounding said oxygen pump and oxygen concentration cell, said holding member being bonded to said cells for supporting said cells within an exhaust pipe.

* * * * *